US00PP28407P3

(12) United States Plant Patent
Olesen

(10) Patent No.: US PP28,407 P3
(45) Date of Patent: Sep. 19, 2017

(54) ***CLEMATIS* PLANT NAMED 'EVIPO074'**

(50) Latin Name: *Clematis viticella*
Varietal Denomination: Evipo074

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 56 days.

(21) Appl. No.: 14/756,261

(22) Filed: Aug. 20, 2015

(65) Prior Publication Data

US 2017/0055419 P1 Feb. 23, 2017

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS http://poulsenroser.com/media/63344/Clematis-2012-2013_Poulsen-Roser_LR_GBP.pdf, "Perfection by Poulsen *Clematis* Main varieties 2013".*
UPOV hit on *Clematis* plant named 'Evipo074', QZ PBR 43294, published Dec. 15, 2014.*

* cited by examiner

*Primary Examiner* — Anne Grunberg

(57) ABSTRACT

A new *Clematis* plant with a compact growth habit, profuse, violet purple flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

1 Drawing Sheet

Botanical classification:
Genus: *Clematis.*
Species: *viticella.*
Variety denomination: 'Evipo074'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2003 and the resulting seeds were planted the following winter in a controlled environment in Guernsey, Channel Islands, United Kingdom. The new variety named 'Evipo074' originated as a single seedling from the stated cross.

The new *clematis* plant may be distinguished from its female seed parent and male pollen parent by the following characteristics. The female seed parent has flowers which are red-purple, while the new variety has flowers which are lavender blue with a red-purple central bar. The male pollen plant has flowers which are red-purple.

The objective of the hybridization of this *clematis* plant was to create a new and distinct variety for nursery culture with unique qualities such as:

1. Uniform and abundant violet purple flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo074' was selected by Mogens N. Olesen and Raymond J. Evison in their *clematis* development program in the Channel Islands, United Kingdom in 2004. Asexual reproduction of 'Evipo074' by means of vegetative cuttings and traditional layering was first performed by Mogens N. Olesen and Raymond J. Evison in the nursery during the summer of 2004. This initial and subsequent asexual propagations have demonstrated that the characteristics of 'Evipo074' are true to type and are transmitted from one generation to the next.

BRIEF DESCRIPTION OF THE DRAWING

The accompanying color illustration shows as true as is reasonably possible to obtain in color photographs of this type the typical characteristics of the buds, flowers, leaves, and stems, of 'Evipo074'. Specifically illustrated in the drawing are flowers at various stages of development, flower in parts, juvenile stem and leaves, mature leaves, and a stem exhibiting flower buds, partially opened flowers, and leaves. Plants shown are 2 years of age.

DETAILED DESCRIPTION OF THE VARIETY

The following is a detailed description of 'Evipo074', as observed in its growth throughout the flowering period in Yamhill County Oreg. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo037' described and illustrated in U.S. Plant Pat. No. 18,104 are compared to 'Evipo074' in Chart 1.

CHART 1

| | 'Evipo074' | 'Evipo037' |
|---|---|---|
| Flower diameter | 135 mm | 130 to 150 mm |
| Tepal upper surface | Violet Group N88A with a central bar Violet Group N79B | Violet-Blue Group N89C |
| Tepal count | 6 | 6 to 7 tepals |

Flower and Flower Bud

Blooming habit: Continuous. The natural flowering period is generally from April to September.

Flower bud:
- *Size*.—Normally 40 mm in length. Bud diameter is 17 mm.
- *Bud form*.—Elliptic, somewhat urceolate.
- *Texture*.—Pubescent.
- *Bud color*.—Yellow-Green Group 145A.

Peduncle:
- *Surface texture*.—Smooth.
- *Length*.—On average 20 mm.
- *Diameter*.—2 mm.
- *Color*.—Yellow-Green Group 144B.
- *Strength*.—Moderately strong.

Receptacle:
- *Surface texture*.—Lightly pubescent.
- *Shape*.—Broad funnel.
- *Size*.—1 mm (h)×3 mm (w).
- *Color*.—Yellow-Green Group 144B.

Flower arrangement:
- *Location on vine*.—New and old growth.
- *Borne*.—Each flowering branch develops 3 to 7 flower buds.

Flower bloom:
- *Size*.—On average, flowers are 135 mm in diameter and 25 mm in depth.
- *Profile*.—Open flowers are almost flat.
- *Fragrance*.—None.
- *Lasting quality*.—Flowers normally remain up to 10 days on the plant.

Tepals:
- *Tepal color*.—Upon opening, the upper surface is Violet Group N88A with a central bar Violet Group N79 B. Lower surface is Violet Group 86A with overlay of Violet-Blue Group 91B and a central bar Yellow-Green Group 145C. After opening, the upper surface is Violet Group N88A with a central bar of Violet Group N79B. The lower surface is Violet Group 86A with overlay of Violet-Blue Group 91B and a central bar Yellow-Green Group 145C.
- *Quantity*.—Normally 6 tepals.
- *Size*.—About 65 mm in length by 30 mm wide.
- *Shape*.—Individual tepal shape is ovate/lanceolate/oblanceolate/obovate/elliptic/spatulate. The tepal apex is acuminate/mucronate/rounded. The tepal base is typically acute/rounded.
- *Apex recurvature*.—Slight.
- *Tepal cross section*.—Slightly cupped.
- *Margins*.—Entire. Strong to moderate, tight undulations.
- *Persistence*.—Tepals drop off cleanly.

Reproductive organs:
- *Arrangement*.—Open.
- *Pollen*.—None observed.
- *Anthers*.—Size: 5 mm in length. Color: Black Group 202A. Quantity: On average, 45.
- *Filaments*.—Color: Violet-Blue Group 91A at the base, and Purple Group 76D. Length: 10 mm.
- *Pistils*.—Quantity: On average, 25.
- *Styles*.—Color: White Group 155D. Length: 15 mm.

Plant

Plant form: Climbing.

Plant growth: Moderately vigorous.

Size: Seasons growth attains about 60 cm in height. Average spread is 40 cm.

Stems:
- *Color*.—Juvenile stems are Yellow-Green Group 144B. Mature stems are Greyed-Purple 183C.
- *Internodes*.—On average, 60 cm between nodes.
- *Length*.—Normally 20 cm from the base of the plant to the flowering portion of the stem.
- *Diameter*.—2 or 3 mm.
- *Texture*.—Mature stems are generally smooth.

Plant foliage:
- *Leaf characteristics*.—Deciduous.
- *Arrangement*.—Trifoliate.
- *Leaf size*.—Compound leaves are normally 140 mm (l)×120 mm (w). Leaflets are normally 45 mm (l)×25 mm (w).
- *Abundance*.—On average 1 or 2 leaves per 10 cm of stem.
- *Leaf color*.—Juvenile upper Yellow-Green Group 144A. Juvenile lower Yellow-Green Group 144B. Mature upper Yellow-Green Group 146A with marginal intonations of Greyed-Red Group 178A. Mature, lower leaflets are Yellow-Green Group 146C.
- *Stipules*.—Absent.
- *Petioles*.—Size: Normally 60 mm in length by 1 mm diameter. Texture: Smooth. Color: Greyed-Purple Group 187A.
- *Petioloule*.—Size: Normally 10 mm in length by 1 mm diameter. Texture: Smooth. Color: Greyed-Purple Group 187A.
- *Leaflet shape*.—Elliptic. The base is rounded. The apex is acute.
- *Margin*.—Entire.
- *Texture*.—The upper and lower surfaces are smooth.
- *Thickness*.—Average.
- *Glossiness*.—Somewhat glossy.

Disease resistance: Subject to any disease that normally attacks the species. However the variety is more tolerant to *clematis* wilt, *Ascochyta clematidina*, than some *clematis* known to the inventors.

Cold hardiness: The variety is tolerant to USDA Hardiness Zone 6.

Heat tolerance: The variety has been found to be suitable for climate conditions found in the American Horticulture Society heat zone 7.

I claim:

1. A new and distinct variety of *clematis* plant named 'Evipo074', substantially as described and illustrated, due to its abundant violet purple flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

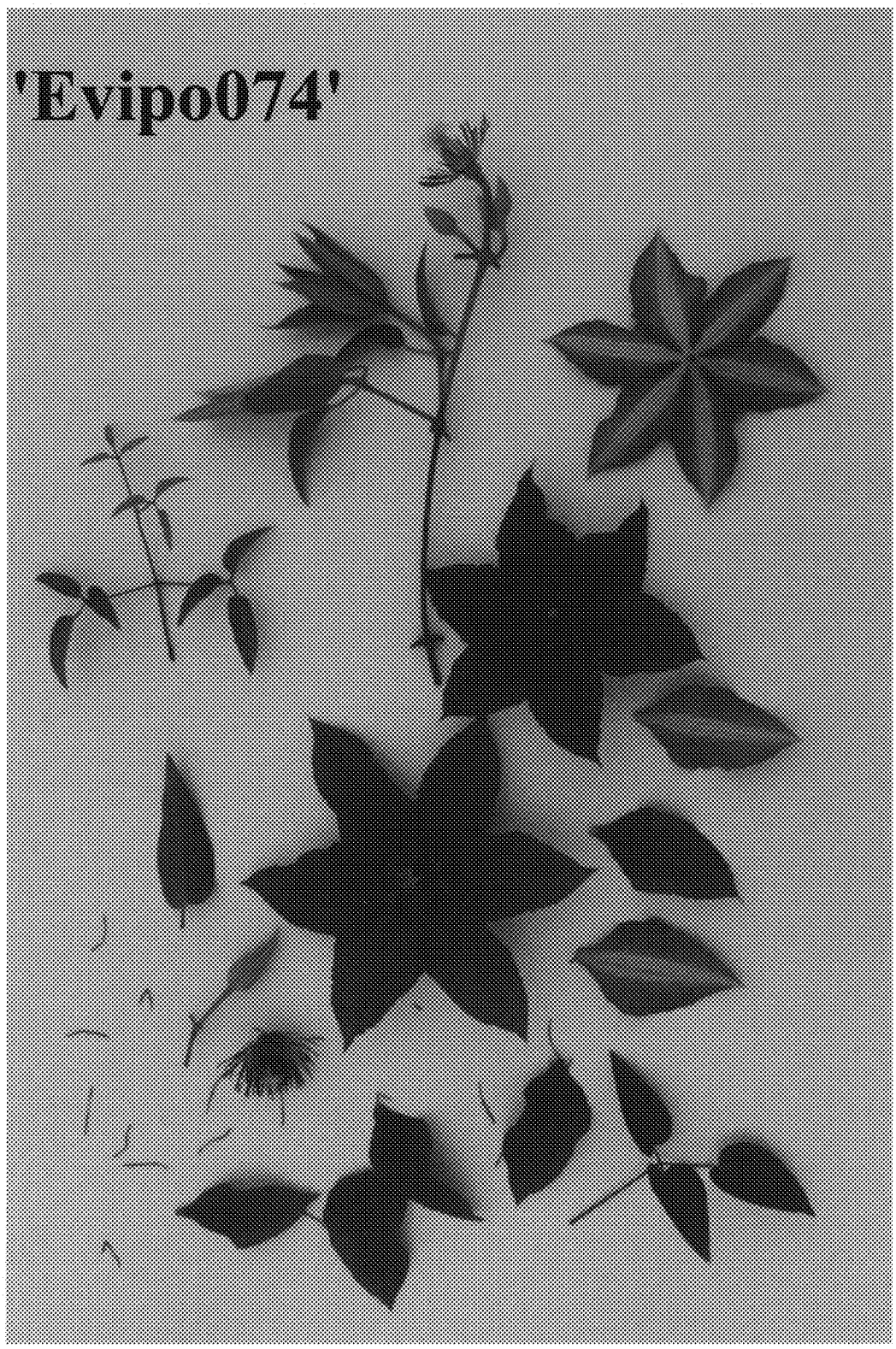
'Evipo074'